United States Patent [19]

Weissman et al.

[11] Patent Number: 5,556,001
[45] Date of Patent: Sep. 17, 1996

[54] MIXING APPARATUS FOR FLUIDS OPERATIVE FROM A PRESSURIZED LIQUID 1 SUPPLY-DESIGN I

[76] Inventors: William R. Weissman, 4418 Vineland Ave., North Hollywood, Calif. 91602; Peter Liapis, 7188 Sunset Blvd. Suite 204, Los Angeles, Calif. 90069; George Sanchez, 22201 Ventura Blvd.; Bernardo Baran, 22201 Ventura Blvd., both of Woodland Hills, Calif. 91364

[21] Appl. No.: 255,703

[22] Filed: Jun. 7, 1994

[51] Int. Cl.⁶ .................................................. E03C 1/04
[52] U.S. Cl. ............................. 222/1; 222/133; 222/334; 222/129.2
[58] Field of Search .......................... 222/1, 129, 129.2, 222/133, 134, 135, 334; 128/66, 629, 200.21; 604/131, 149, 150, 151, 181, 183, 257; 239/322, 332, 329; 417/181, 264, 392; 4/628, 638

[56] References Cited

U.S. PATENT DOCUMENTS

| | | | |
|---|---|---|---|
| 2,625,430 | 1/1953 | Murphy | 222/129.2 X |
| 2,736,466 | 2/1956 | Rodth | 222/129.2 X |
| 2,743,847 | 5/1956 | Pollak | 222/133 |
| 2,744,789 | 5/1956 | Sutton | 222/133 |
| 2,867,230 | 1/1959 | Bletcher et al. | 137/119 |
| 3,006,509 | 10/1961 | Fuller | 222/133 |
| 3,182,860 | 5/1965 | Gallo, Sr. | 222/129.2 X |
| 3,225,759 | 12/1965 | Drapon et al. | |
| 3,500,824 | 3/1970 | Gilbert | |
| 4,043,337 | 8/1977 | Baugher | 128/229 |
| 4,141,467 | 2/1979 | Augustijn et al. | 222/133 X |
| 4,166,084 | 8/1979 | Shea | 222/133 X |
| 4,265,229 | 5/1981 | Rice | 128/66 |
| 4,452,238 | 6/1984 | Kerr | 222/133 X |
| 4,564,005 | 1/1986 | Merchand | 128/66 |
| 4,793,331 | 12/1988 | Stewart | 128/66 |
| 4,815,634 | 3/1989 | Nowicki | 222/133 |
| 4,967,936 | 11/1990 | Bingler | 222/129.2 |
| 4,979,503 | 12/1990 | Chernack | |
| 5,218,956 | 6/1993 | Handler et al. | |

*Primary Examiner*—Andres Kashnikow
*Assistant Examiner*—Kenneth R. DeRosa

[57] ABSTRACT

An apparatus (20, 60) capable of dispensing a liquid 1 (e.g. water) or a liquid 1/liquid 2 mixture through a hand held syringe (26) and configured, in embodiments thereof, to be attached to a showerhead (24) or sink faucet (68) is provided. Liquid 2 (e.g. a dental concentrate) is held in a container (140) and dispensed by liquid 1 pressure on a piston (142) therein. A spool valve (84) responsive to a liquid 1 pressure bleed line (110a, 110b) diverts liquid 1 from the showerhead or sink faucet to drive the piston. The apparatus is controlled by a mode control disc (30) mounted in the syringe. Provisions for adjusting the flow rate of the dispensed liquid (34) and the proportional mix of the liquid 1/liquid 2 mixture (160) are provided.

20 Claims, 3 Drawing Sheets

MIXING APPARATUS FOR FLUIDS OPERATIVE FROM A PRESSURIZED LIQUID 1 SUPPLY-DESIGN I

TECHNICAL FIELD

The present invention relates generally to fluid mixing apparatus and more particularly to apparatus for mixing and applying an irrigating stream.

BACKGROUND ART

Mixing apparatus for generating and applying a stream of liquid (e.g. water, soap mixture, alcohol, disinfectant, industrial cleanser) find particular utility in irrigating recessed areas which are otherwise difficult to reach.

Such apparatus generally provide a handheld syringe terminating in an orifice which facilitates directing the liquid stream about the object to be irrigated. A user typically must use the other hand to operate an electrical switch to energize the generator. They typically are capable of applying only one liquid, that being one placed in an internal container, and do not allow the concentration of this liquid to be adjusted, i.e. it cannot be adjustably diluted (e.g. with water) to reduce consumption.

An exemplary application of such apparatus is the irrigating of spaces between teeth and gums at home or in a dental office. Apparatus configured specifically for this application typically employ electrically powered pumps which introduces the presence of a high voltage apparatus into an environment having excellent electrical grounds close at hand (e.g. sink taps, shower pipes) which is a combination dangerous to the user.

DISCLOSURE OF INVENTION

The present invention is directed to liquid 1 pressure powered apparatus for generating and directing an irrigating stream.

Apparatus in accordance with the invention are characterized by a liquid 2 dispenser configured to be responsive to a diverter valve interposed between a liquid supply inlet and outlet. A syringe is configured to control the diverter valve and control flow of liquids 1 and 2 from the dispenser and diverter valve.

In accordance with a feature of the invention the apparatus is configured to mix liquids 1 and 2 to a proportion selected by the user and to dispense either liquid 1 or a liquid 3 which is a liquid 1 and 2 mixture as selected by the user.

In accordance with another feature of the invention, the apparatus is entirely powered by liquid 1 pressure enabling it to be safely used in moist environments (e.g. home showers, industrial cleaning booths).

In a preferred embodiment a spool valve responsive to a liquid 1 pressure bleed line is used to divert liquid 1 to a piston actuated dispenser.

The novel features of the invention are set forth with particularity in the appended claims. The invention will be best understood from the following description when read in conjunction with the accompanying drawings.

MODES FOR CARRYING OUT THE INVENTION

Figure 1:
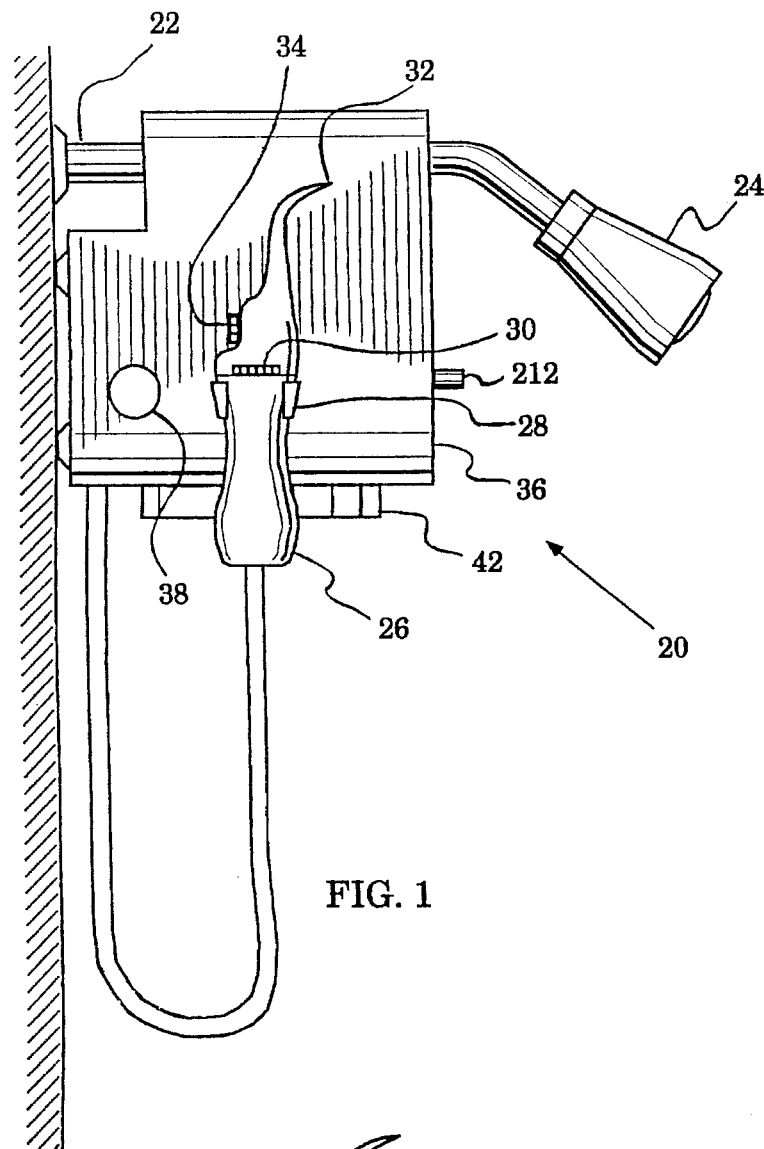
FIG. 1 is an elevation view of a preferred apparatus embodiment, in accordance with the present invention, mounted at a showerhead.

FIG. 1 is an elevation view of an apparatus 20, in accordance with the present invention, interposed between a liquid 1 (e.g. water) supply inlet 22 and a showerhead 24. The apparatus 20 has a hand held syringe 26 which may be removed from a holder 28. A mode control disc 30 is used to control the apparatus between a non-dispensing and a dispensing mode. In the non-dispensing mode liquid 1 issues from the showerhead 24 and the syringe 26 may be left in the holder 28. In the dispensing mode the mode control disc 30 may be set to positions in which liquid 1 or a mixture (liquid 3) of liquid 1 and a liquid 2 concentrate issues from the orifice 32. In the dispensing mode water does not issue from the showerhead 24.

Also located on the syringe 26 is an flow adjustment knob 34 which is used to adjust the flow rate of the liquid 1 or 3 issuing from the orifice 32. Disposed on the apparatus body 36 is a mixture adjustment knob 38 which changes the proportional mix of the liquid 3 that is dispensed from the orifice 32.

The flow and mixture adjustments (knobs 34, 38) are made only occasionally. Once they have been set to the user's satisfaction, the use of the apparatus 20 is simple. For normal use of the showerhead 24, the syringe 26 is left in the holder 28 with the mode control disc 30 in the non-dispensing setting. To use the syringe 26, it is lifted from the holder 28 and set in either the liquid 1 dispensing position or the liquid 3 dispensing position by moving the mode control disc 30 appropriately. One can alternate between use of the showerhead 24 and the syringe 26 by simple movement of the mode control disc 30.

Thus, for example, teeth and gums may be effectively irrigated without the handling of tubes or other concentrate containers. Irrigating with the syringe 26 is a simple maneuver accomplished while taking a shower or bath and cleanup is almost nonexistent. Only occasionally is it necessary to unscrew a concentrate container 42 from the bottom of the body 36 and refill it with liquid concentrate.

Figure 2:
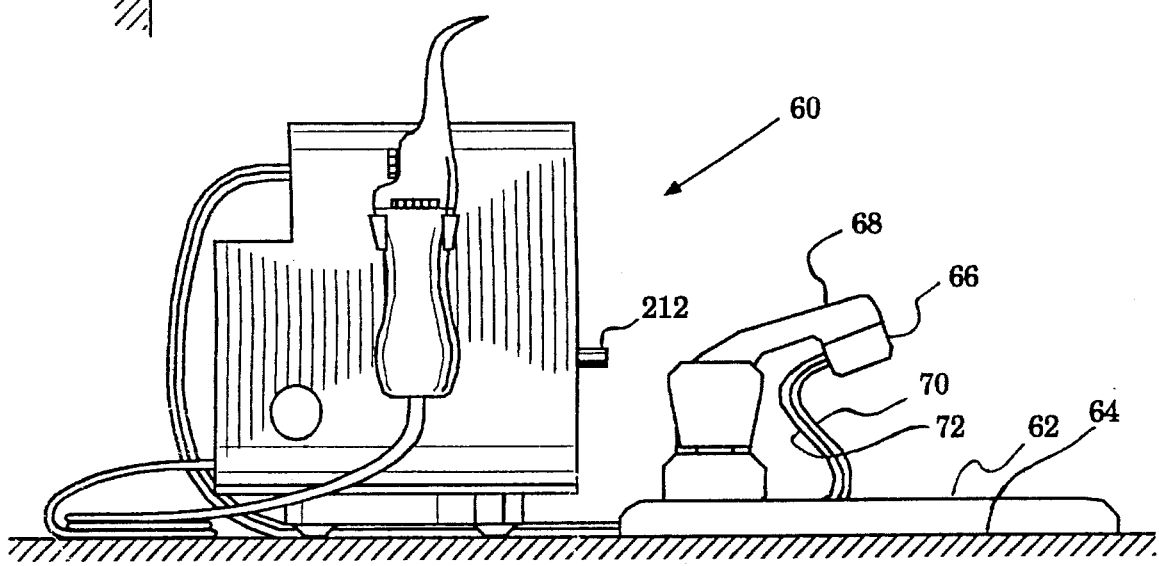
FIG. 2 is an elevation view of another preferred embodiment mounted at a bathroom faucet.

FIG. 2 is an elevation view of another apparatus 60 in association with a bathroom sink 62 and countertop 64. The apparatus 60 is similar to the apparatus 20 and differs primarily in its disposition with the liquid 1 supply. A standard faucet adaptor 66 is used at the faucet head 68 to interpose the apparatus 60 between a liquid 1 supply inlet 70 and a liquid 1 supply outlet 72. In other respects the functioning of the apparatus 60 is the same as that of the apparatus 20.

FIGS. 1 and 2 illustrate embodiments of the invention configured for a specific application, i.e. irrigating the teeth and gums in a home environment. Generally, however, apparatus in accordance with the invention will find application and utility for irrigating hard to access areas in a variety of environments, e.g. home, factory, medical office, veterinarian office. Examples of such applications include cleaning of ears, electrical circuit board cleaning, surgical cleaning, and use as a douche.

Apparatus in accordance with the invention may be configured to generate a stream of liquid 1 or a liquid 3 comprising a liquid 2 concentrate and the liquid 1. Examples of a liquid concentrate include alcohol, industrial cleaner, disinfectant and concentrates directed to dental irrigating. Thus it should be understood that the description of the embodiments 20, 60 are exemplary of the variety of configurations, and uses thereof, in which the invention may be realized. In these specific embodiments, liquid 1 is water and liquid 2 is a dental dentifrice.

Figure 3:
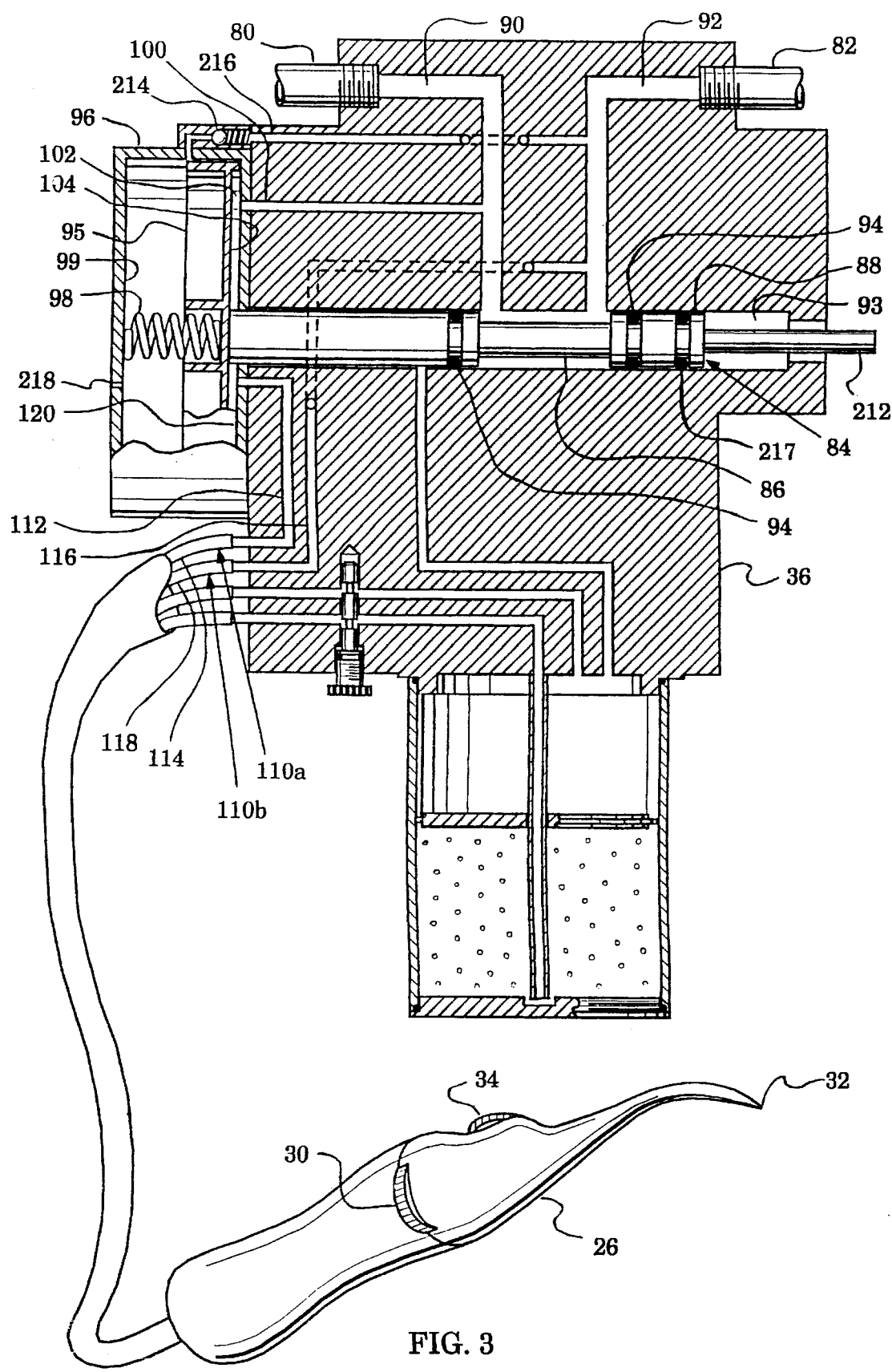
FIG. 3 is a schematic of the apparatus of FIGS. 1 and 2 illustrating a non-dispensing mode.

Attention is now directed in detail to FIG. 3 which is a schematic of the apparatus 20, 60 illustrating the structure and functioning thereof in the non-dispensing mode. The body 36 is represented in section and shows a liquid 1 supply inlet 80 and a liquid 1 supply outlet 82 inserted therein. A diverter spool valve 84 is shown in the non-dispensing mode in which the recessed portion 86 of the spool 88 allows communication between the supply inlet 80 and the supply outlet 82 by way of bores 90, 92 and 93.

The spool 88 slides within bore 93 and is sealed thereto by O rings 94. It is attached at one end to a piston 95 disposed within a cylinder 96. The piston 94 is urged to the non-dispensing position by a spring 98 bearing against a wall 99 of the cylinder 96.

The liquid 1 supply inlet 80 communicates by means of a supply line, defined by bores 90 and 100, with the chamber 102 defined between the cylinder 96 and the face 104 of the piston 95. The chamber 102 is connected to the supply outlet bore 92 by a liquid 1 pressure bleed line. The bleed line is comprised of a first bleed line 110a running from the chamber 102 to the syringe 26 and a second bleed line 110b running from the syringe 26 to the outlet supply bore 92. The first bleed line 110a includes bore 112 and flexible tube 114. The second bleed line 110b includes bore 116 and flexible tube 118 (bore 116 is shown in dashed lines in areas where it passes under other bores).

In the non-dispensing mode illustrated in FIG. 3 the first bleed line 110a is connected through the syringe 26 to the second bleed line 110b (details of this connection are disclosed below in the description of FIG. 4). Because the liquid 1 pressure in the showerhead 24 or the faucet 68 is low, this bleed line connection relieves pressure in the chamber 102 and consequently the piston 95, under urging of the spring 98, abuts the cylinder face 120. Thus, in the non-dispensing mode, a passage remains open from the supply inlet 80 to the supply outlet 82.

Figure 4:
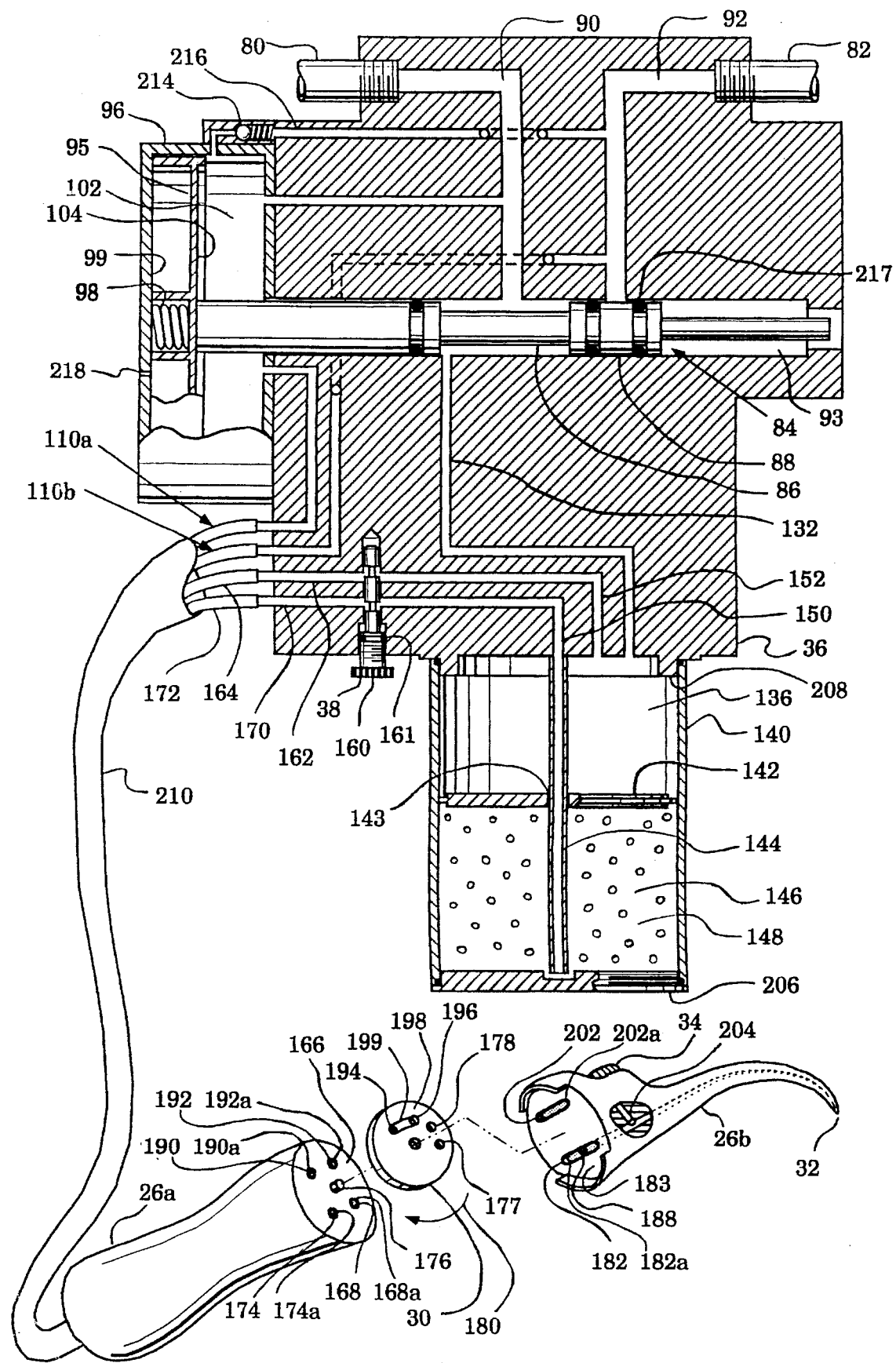
FIG. 4 is a schematic of the apparatus of FIGS. 1 and 2 illustrating a dispensing mode.

FIG. 4 is a schematic, similar to FIG. 3, illustrating the dispensing mode of the apparatus (20, 60 of FIGS. 1, 2). In FIG. 4 the syringe 26 has been disassembled into a handle 26a, a mode control disc 30 and a tip 26b defining the orifice 32. In the dispensing mode the first bleed line 110a and the second bleed line 110b are interrupted, as will be explained below, at their juncture in the syringe 26. As a result the pressure in the chamber 102 is not relieved and the cylinder 95 is urged, against the urging of the spring 96 to abut the wall 99. In this position the recessed portion 86 of the spool 88 connects, through bores 90, 93 and 132, the supply inlet 80 to the chamber 136 within container 140. Bore 132 thereby defines a diverter outlet from the spool valve 84.

A piston 142 has a hole 143 therein which receives a rigid tube 144 mounted in the body 36. Liquid 1 pressure bears on the piston 142 and liquid 2 (dentifrice) 146 in the chamber 148 below the piston 142 is urged thereby to flow up the tube 144 into bore 150.

Thus, in the dispensing mode liquid 1 and liquid 2 are separately urged in, respectively, bores 152 and 150 past a differential flow rate adjustment spool valve 160 (the mixture adjustment knob 38 of FIG. 1 is attached thereto). Each of the bores 150, 152 correspond with one of two recessed portions in the spool valve 160. The spool valve is rotatably threaded into the body 36 and sealed thereto with an O ring 161. The recessed portions are arranged so that when one is aligned with one of the bores 150,152, the other is misaligned with the other of the bores. Thus when one bore has been fully restricted the other has been minimally restricted.

Liquid 1 is carried past the spool valve 160 through bore 162 and flexible conduit 164 to a face 166 of the syringe handle 26a where the conduit 164 terminates in a port 168 surrounded by an O ring 168a. Similarly, liquid 2 is carried past the spool valve 160 in bore 170 and flexible conduit 172 to terminate at the face 166 in a port 174 surrounded by an O ring 174a.

Mode control disc 30 is rotatably mounted on a pin 176 projecting from the face 166 and has a pair of holes 177, 178. It can be seen that, as the mode control disc is turned in direction 180, hole 177 can be aligned with port 168. This movement will also align the hole 177 with the recessed mixing chamber 182 in face 183 of the syringe tip 26b. The mixing chamber 182 is surrounded with an O ring 182a and communicates through a narrowing tube 188 with the orifice 32. When the handle 26a, disc 30 and tip 26b are assembled the faces of the disc 30 abut the O rings 168a and 174a. Thus liquid 1 1s restrained to flow through hole 177 and issue from the orifice 32. For reference purposes, this position of the mode control disc 30 will be denoted position 2.

If the mode control disc 30 is turned further in direction 180 the holes 177, 178 will be aligned with, respectively, ports 174, 168. This is denoted position 3 and in this position liquid 1 and liquid 2 are restrained to flow through, respectively, holes 178, 177 into the mixing chamber 182. Thus in position 3 of the mode control disc 30, liquid 1 and liquid 2 mix in the chamber 182 and then issue through orifice 32. In this position the proportional mix of liquid 1 and liquid 2 that issues from the orifice 32 may be changed by adjusting the proportional flow rate spool valve 160. Since the spool valve 160 controls the relative flow rates it effectively changes the proportional mix at the mixing chamber 182.

The first bleed line 110a and second bleed line 110b, described above relative to FIG. 3, terminate, respectively, at the face 166 in ports 190, 192 ringed by O rings 190a, 192a. When the mode control disc 30 is in positions 2 and 3 described above, the hole 194 in the disc 30 does not align with port 190. Thus the O ring 190a is abutted by the disc 30 and the bleed line comprised of first and second bleed lines 110a, 110b is interrupted. This keeps the spool valve 88 in the position shown in FIG. 4.

A final position, which can be denoted position 1, of the mode control disc 30 is shown in FIG. 4 where hole 194 and a second hole 196 align with, respectively, ports 190,192. The face 198 of the mode control disc 30 defines a slot 199 that connects holes 194, 196. The face 183 of the tip 26b defines a corresponding groove 202 surrounded by an O ring 202a. In position 1 the first bleed line 110a and second bleed line 110b are connected through holes 194, 196 and the space defined by slot 199 and groove 202. Thus position 1 of the control disc 30 activates the non-dispensing mode illustrated in FIG. 3 while positions 2 and 3 activate the dispensing mode illustrated in FIG. 4.

The flow adjustment knob 34, shown in FIG. 4, is attached to a body that is threadably mounted in the tip 26b and terminates in a pin 204. Thus the knob 34 can be rotated to cause pin 204 to protrude into tube 188 to reduce flow from the orifice 32.

The container 140 is internally threaded at the upper and lower margins thereof. A lid 206 and a protruding ring 208 of the body 36 are correspondingly threaded. Thus the lid 206 can be placed on the container 140, the container filled with dentifrice, the piston 142 placed therein and the assembly mounted on the ring 208. The ring 208 and the lid 206 carry O rings to seal against the container 140.

The conduits 164, 172 and first and second bleed lines 110a, 110b are covered by a flexible sheath 210.

In FIG. 3 (and FIGS. 1, 2) it may be seen that the spool 88 terminates in a tip 212 protruding out through the body 36. The tip 212 may be used to free the spool valve 84 and attached piston 95 1f they become fixed within the body 36 because of a buildup of soap film or other foreign matter.

As shown in FIGS. 3 and 4, chamber 102, formed by cylinder 96 and the face 104 of piston 95, is connected past a ball check valve 214 and through bores 216 and 92 to the supply outlet 82. Excessive liquid 1 pressure from the supply inlet 80 will open the check valve 214 to the supply outlet 82 and, thereby, protect the apparatus from damage. An O ring 217 in the spool valve 84 prevents liquid 1 from exiting through bore 93.

The piston 94 fits closely within the cylinder 96 to prevent liquid 1 from bypassing it. Due to this close fit it is necessary, as shown in FIGS. 3 and 4, to have an orifice 218 in the cylinder 96, located behind the piston 95, to vent it to atmospheric pressure.

From the foregoing it should now be recognized that exemplary apparatus embodiments have been disclosed herein configured specifically for cleansing of teeth and gums. Generally, however, embodiments of the invention may be configured for generating a stream of liquid 1 or 3 for irrigating of any restricted access area. Although the described preferred embodiments have an orifice configured to define a fine stream of liquid it should be understood that the orifice may generally assume any shape. Apparatus in accordance with the present invention operate solely with liquid 1 pressure and are, therefore, safe to use in any moist environment.

Although the present invention has been described with reference to preferred embodiments, numerous modifications and rearrangements can be made with the equivalent result still embraced within the scope of the invention.

What is claimed is:

1. A method for dispensing liquid 1 and liquid 2 from an orifice, comprising the steps of;
   interposing a diverter valve between a liquid 1 supply inlet and a liquid 1 supply outlet wherein said diverter valve is configured to connect, in a first position thereof, said supply inlet and said supply outlet, and, in a second position thereof, a diverter outlet therefrom and said supply inlet;
   configuring said diverter valve to move from said first valve position to said second valve position when a pressure bleed line is interrupted;
   urging, with liquid 1 from said diverter outlet, a dispenser piston against liquid 2 in a container to dispense it therefrom;
   conducting, separately, said liquid 1 and said liquid 2 from, respectively, said diverter outlet and said container, to a syringe defining an orifice therefrom;
   selecting, with a control valve in said syringe that interrupts said bleed line, between said first position and said second position of said diverter valve; and
   controlling, with said control valve, the flow of said liquid 1 and said liquid 2 from said orifice.

2. A method as defined in claim 1 further comprising the steps of:
   adjusting, differentially, the flow rate of said liquid 1 and said liquid 2; and
   mixing said liquid 1 and said liquid 2 before dispensing from said orifice.

3. A method as defined in claim 2 wherein said controlling step comprises the steps of:
   configuring a liquid 1 line and a liquid 2 line to conduct said liquid 1 and said liquid 2 to said orifice;
   disposing a rotatable disc defining a pair of holes therein across said liquid 1 line and said liquid 2 line to conduct said liquid 1 and said liquid 2 to said orifice when said pair of holes align therewith.

4. A method as defined in claim 1, wherein said configuring step comprises the steps of:
   defining a spool valve with a piston thereon;
   disposing said piston in a cylinder;
   defining a liquid 1 supply line from said supply inlet to said cylinder; and
   defining a pressure bleed line from said cylinder via said control valve to said supply outlet.

5. Apparatus, comprising:
   a syringe defining an orifice therefrom;
   diverter valve means, interposed between a liquid 1 supply inlet and a liquid 1 supply outlet, adapted to be responsive to liquid 1 pressure relief and defining a diverter outlet, for directing, when in a first valve position, liquid 1 from said supply inlet to said supply outlet and, when in a second valve position, liquid 1 from said supply inlet to said diverter outlet;
   means, containing liquid 2 and connected to said diverter outlet to be responsive to liquid 1 received therefrom, for separately dispensing said liquid 1 and said liquid 2;
   liquid pressure relief means, disposed between said syringe and said diverter valve means, for selecting one of said first valve position and said second valve position; and
   control means, disposed in said syringe between said dispensing means and said orifice, for controlling, via said liquid 1 pressure relief means, the valve position of said diverter valve means and for controlling the flow of said liquid 1 and said liquid 2 from said orifice.

6. Apparatus as defined in claim 6 wherein said dispensing means further comprises means for adjusting the flow rate of said liquid 1 and said liquid 2 dispensed therefrom.

7. Apparatus as defined in claim 5 wherein said dispensing means further comprises conduit means for conducting said liquid 1 and said liquid 2 separately to said control means.

8. Apparatus as defined in claim 5 wherein said diverter valve means comprises;
   a diverter spool valve defining, at an end thereof, a pressure piston;
   a cylinder enclosing said pressure piston;
   a spring urging said diverter spool valve to said first valve position where said diverter spool valve connects said supply inlet to said supply outlet;
   and
   a liquid 1 supply line from said supply input to said cylinder for urging said pressure piston to said second valve position where said diverter spool valve connects said supply inlet to said diverter outlet.

9. Apparatus as defined in claim 8 wherein said pressure relief means comprises a liquid 1 pressure bleed line directed from said cylinder via said control means to said supply outlet whereby said spool valve is urged from said first valve position to said second valve position when said bleed line is interrupted by said control means.

10. Apparatus as defined in claim 5 wherein said dispensing means comprises;

a container holding said liquid 2;

a dispenser piston enclosed by said container and urged, by liquid 1 from said diverter outlet, against said liquid 2;

a liquid 2 passageway from said container; and a liquid 1 passageway communicating with said diverter outlet;

whereby said liquid 1 and said liquid 2 are dispensed from, respectively, said liquid 1 passageway and said liquid 2 passageway when said diverter valve means is in said second valve position.

11. Apparatus as defined in claim 7 wherein said conduit means comprises: a liquid 1 line connecting said liquid 1 passageway and said orifice; and a liquid 2 line connecting said liquid 2 passageway and said orifice.

12. Apparatus as defined in claim 11 wherein said control means comprises a disc defining a hole therethrough, said disc rotatably disposed to intersect said liquid line and said concentrate line to block passage therethrough except when said hole aligns therewith.

13. Apparatus as defined in claim 9 wherein;

said bleed line comprises:

a first bleed line from said cylinder to said syringe; and a second bleed line from said syringe to said supply outlet; and said control means comprises;

a face defining a groove therein; and a disc defining a passage comprising a pair of holes and a slot therebetween;

said disc rotatably disposed abutting said face to connect said first bleed line and said second bleed line when said pair of holes align therewith and said slot aligns with said groove.

14. Apparatus as defined in claim 11 further comprising means, disposed in said syringe, for mixing said liquid 1 and said liquid 2.

15. Apparatus as defined in claim 14 wherein:

said control means comprises a disc defining a pair of holes therethrough, said disc rotatably disposed to complete said liquid 1 line and said liquid 2 line when said pair of holes align therewith; and said mixing means comprises a chamber defined by said syringe and connected to said orifice, Said chamber communicating with said pair of holes when they align with said liquid 1 line and said liquid 2 line.

16. Apparatus as defined in claim 10 wherein said dispensing means further comprises means for adjusting the flow rate of said liquid 1 and said liquid 2 dispensed therefrom.

17. Apparatus as defined in claim 16 wherein said adjusting means comprises an adjustment spool valve having a first annular groove corresponding with said liquid 1 passageway and a second annular groove corresponding with said liquid 2 passageway; said adjustment spool valve disposed such that longitudinal movement thereof restricts one of said liquid 1 passageway and said liquid 2 passageway as it frees the other.

18. Apparatus as defined in claim 10 wherein said said liquid 2 passageway comprises a tube arranged within said container and said dispenser piston defines a hole therein for receiving said tube to be guided thereon.

19. Apparatus, comprising:

a syringe defining an orifice therefrom;

diverter valve means, interposed between a liquid 1 supply inlet and a liquid 1 supply outlet, adapted to be responsive to liquid 1 pressure relief and defining a diverter outlet, for directing, when in a first valve position, liquid 1 from said supply inlet to said supply outlet and, when in a second valve position, liquid 1 from said supply inlet to said diverter outlet;

means, containing liquid 2 and connected to said diverter outlet to be responsive to liquid 1 received therefrom, for separately dispensing said liquid 2 and said liquid 1; and control means, disposed in said syringe between said dispensing means and said orifice, for controlling the valve position of said diverter valve means by providing liquid 1 pressure relief and for controlling the flow of said liquid 1 and said liquid 2 from said orifice.

20. Apparatus as defined in claim 19 wherein said control means comprises liquid 1 pressure relief means, disposed between said syringe and said diverter valve means, for selecting one of said first valve position and said second valve position.

* * * * *